United States Patent
Dermartirosian et al.

(10) Patent No.: US 12,394,612 B2
(45) Date of Patent: *Aug. 19, 2025

(54) DETERMINATION OF ANTIDEPRESSANTS BY MASS SPECTROMETRY

(71) Applicant: Quest Diagnostics Investments LLC, Secaucus, NJ (US)

(72) Inventors: Anita Dermartirosian, Stevenson Ranch, CA (US); Edith Shahbol, Northridge, CA (US); Karin Thomassian, Tujunga, CA (US); Shaun Rezaei, Santa Clarita, CA (US); Asad Shah, Sylmar, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/543,524

(22) Filed: Dec. 18, 2023

(65) Prior Publication Data
US 2024/0120188 A1    Apr. 11, 2024

Related U.S. Application Data

(63) Continuation of application No. 16/887,298, filed on May 29, 2020, now Pat. No. 11,887,828.
(Continued)

(51) Int. Cl.
*H01J 49/00*    (2006.01)
*G01N 30/72*    (2006.01)
*G01N 33/493*   (2006.01)

(52) U.S. Cl.
CPC ........ *H01J 49/004* (2013.01); *G01N 30/7233* (2013.01); *G01N 33/493* (2013.01)

(58) Field of Classification Search
None
See application file for complete search history.

(56) References Cited

U.S. PATENT DOCUMENTS

2014/0047906 A1   2/2014   Herman et al.
2016/0231341 A1   8/2016   Lakshmi et al.
(Continued)

FOREIGN PATENT DOCUMENTS

CN    102175778 A    9/2011
CN    106770857 A    5/2017
(Continued)

OTHER PUBLICATIONS

Saka, C. et al. Determination of Serotonin-Norepinephrine Reuptake Inhibitor Antidepressants in Pharmaceuticals and Biological Material, Critical Reviews in Analytical Chemistry, 43:2-34, 2013 (Year: 2013).*

(Continued)

*Primary Examiner* — Xiaoyun R Xu
(74) *Attorney, Agent, or Firm* — Quest Diagnostics, Inc.

(57) ABSTRACT

A method for detecting or determining an amount of one or more serotonin and norepinephrine reuptake inhibitors (SNRI) and SNRI metabolites in a sample by tandem mass spectrometry includes subjecting the sample to ionization under conditions suitable to produce one or more ions detectable by mass spectrometry; determining the amount of one or more ions by tandem mass spectrometry; and determining the amount of SNRI and SNRI metabolites in the sample based upon the amount of the one or more ions determined by tandem mass spectrometry; and wherein the one or more SNRI and SNRI metabolites includes duloxetine.

16 Claims, 12 Drawing Sheets

Related U.S. Application Data

(60) Provisional application No. 62/855,863, filed on May 31, 2019.

(56) References Cited

U.S. PATENT DOCUMENTS

| | | | |
|---|---|---|---|
| 2016/0370388 A1 | 12/2016 | Reisinger | |
| 2017/0168029 A1 | 6/2017 | Herman et al. | |
| 2018/0017580 A1 | 1/2018 | Kaldate | |
| 2018/0267015 A1 | 9/2018 | Meyer | |

FOREIGN PATENT DOCUMENTS

| | | |
|---|---|---|
| CN | 109085263 A | 12/2018 |
| CN | 109085264 A | 12/2018 |
| WO | 2016205285 A1 | 12/2016 |
| WO | 2018078017 A1 | 5/2018 |
| WO | 2018078018 A2 | 5/2018 |

OTHER PUBLICATIONS

Dubey, S. et al. Rapid sensitive validated UPLC-MS method for determination of venlafaxine and its metabolite in rat plasma: Application to Pharmacokinetic Study, Journal of PharmaceuticalAnalysis, 2013;3(6):466-471 (Year: 2013).*

Brazdova, B., et al., "Screening and Quantification of Multiple Drugs in Urine Using Automated Online Sample Preparation and Tandem Mass Spectrometry," Thermo Scientific, vol. 512, 2 pages. Clinical Research and Forensic Toxicology Application Compendium Endocrine Analysis for Clinical Research, Therapeutic Drug Analysis for Clinical Research Drugs of Abuse Analysis for Forensic Toxicology Pain Management Drug Analysis for Forensic Toxicology Endocrine Endocrine Endocrine Therapeutic, 2014, p. 374.

Extended European Search Report for Application No. 20813677.0, mailed on Jul. 28, 2023, 10 pages.

Final Office Action mailed Dec. 9, 2022 for U.S. Appl. No. 16/887,298, filed May 29, 2020.

International Search Report and Written Opinion for Application No. PCT/US2020/035233, mailed on Sep. 17, 2020, 8 Pages.

Lin et al., "Method Validation of a Tricyclic Antidepressant Drug Panel in Urine by UPLC-MS/MS," Annals of Clinical Laboratory Science, 2014, vol. 44 (4), pp. 431-436.

Non-Final Office Action mailed Jun. 26, 2023 for U.S. Appl. No. 16/887,298, filed May 29, 2020.

Non-Final Office Action mailed May 26, 2022 for U.S. Appl. No. 16/887,298, filed May 29, 2020.

Salgado-Petinal, C., et al., "Rapid Screening of Selective Serotonin Re-Uptake Inhibitors in Urine Samples Using Solid-phase Microextraction Gas Chromatography-Mass Spectrometry," Analytical and Bioanalytical Chemistry, 2005, vol. 382, pp. 1351-1359.

Weisskopf, E., et al., "Simultaneous Determination of Selective Serotonin Reuptake Inhibitors and Their Main Metabolites in Human Breast Milk by Liquid Chromatography-Electrospray Mass Spectrometry," Journal of Chromatography B, 2017, vol. 1057, pp. 101-109.

Jingying, et al., Simultaneous Determination of Blood Drug Concentrations of 7 Antidepressants and 5 Antipsychotic Drugs by Liquid Chromatography-tandem Mass Spectrometry, Chinese Journal of Drug Applications and Monitoring 2010, vol. 7(5), pp. 272-275.

Yin, L., et al., "A Parallel-Column LC-MS/MS Method for High-Throughput Analysis of Eight Antiepileptic Drugs in Clinical Therapeutic Drug Monitoring," Chromatographia, 2017, vol. 80, pp. 137-143.

* cited by examiner the invention

DETERMINATION OF ANTIDEPRESSANTS BY MASS SPECTROMETRY

CROSS-REFERENCE TO RELATED PATENT APPLICATIONS

This application is a continuation application of U.S. application Ser. No. 16/887,298, filed May 29, 2020, which claims benefit of U.S. Provisional Application No. 62/855,863, filed May 31, 2019, each of which is incorporated by reference herein in its entirety.

BACKGROUND OF THE INVENTION

Baseline testing is useful to help clinicians determine patient use or non-use of an antidepressant drug or drugs prior to treatment. It is crucial to monitor patients who are prescribed antidepressants to ensure compliance and avoid unintended polydrug use. Some antidepressants, such as selective serotonin reuptake inhibitors (SSRIs), may have harmful side effects and should not be mixed with drugs within the same class. An accurate testing for antidepressant and metabolites is needed.

SUMMARY OF THE INVENTION

In one aspect, provided herein are methods for detection and quantitation of antidepressants and antidepressant metabolites by mass spectrometry.

Provided herein are methods for detecting the presence or amount of antidepressants and/or antidepressant metabolites in a sample by mass spectrometry. The methods include subjecting the sample to ionization under conditions suitable to produce one or more ions detectable by mass spectrometry; determining the amount of one or more ions by mass spectrometry; and using the amount of one or more ions to determine the presence or amount of antidepressants and/or antidepressant metabolites in the sample.

In some embodiments, mass spectrometry comprises tandem mass spectrometry. In these embodiments, the methods include: a) ionizing the sample under conditions suitable to produce a precursor ion; b) fragmenting a precursor ion to produce one or more fragment ions; c) determining the amount of one or more ions produced in steps a) and b); and d) using the amount of the one or more ions determined in step c) to determine the presence or amount of antidepressants and metabolites in the sample.

In some embodiments, provided herein are methods for detecting or determining the amount of one or more antidepressants and antidepressant metabolites comprising selective serotonin reuptake inhibitors, serotonin and norepinephrine reuptake inhibitors, norepinephrine and dopamine reuptake inhibitors, tricyclic antidepressants, sedatives, and/or antidepressant metabolites metabolites.

In some embodiments, provided herein are methods for detecting or determining the amount of one or more antidepressants and antidepressant metabolites selected from the group consisting of fluoxetine, paroxetine, sertraline, citalopram, escitalopram, fluvoxamine, vilazodone, duloxetine, venlafaxine, desmethylvenlafaxine, hydroxybupropion, imipramine, nortriptyline, amitriptyline, doxepin, trimipramine, desipramine, protriptyline, amoxapine, clomipramine, maprotiline, trazodone, mirtazapine, vortioxetine, desmethylcitalopram, desmethylclomipramine, desmethyldoxepin, norfluoxetine, norfluvoxamine, norsertraline, and 1,3-chlorophenylpiperazine.

In some embodiments, provided herein are methods for detecting or determining the amount of one or more selective serotonin reuptake inhibitors (fluoxetine, paroxetine, sertraline, citalopram, escitalopram, fluvoxamine, vilazodone); serotonin and norepinephrine reuptake inhibitors (duloxetine, venlafaxine, desmethylvenlafaxine); norepinephrine and dopamine reuptake inhibitors (hydroxybupropion); tricyclic antidepressants (imipramine, nortriptyline, amitriptyline, doxepin, trimipramine, desipramine, protriptyline, amoxapine, clomipramine, maprotiline). Other antidepressants used in this assay also act as sedatives and are trazodone, mirtazapine and vortioxetine. Metabolites tested were desmethylcitalopram, desmethylclomipramine, desmethyldoxepin, norfluoxetine, norfluvoxamine, norsertraline, and 1,3-chlorophenylpiperazine.

In some embodiments, provided herein are methods for simultaneously detecting or determining the amount of 10 or more antidepressants and antidepressant metabolites.

In some embodiments, provided herein are methods for simultaneously detecting or determining the amount of 20 or more antidepressants and antidepressant metabolites.

In some embodiments, provided herein are methods for simultaneously detecting or determining the amount of 30 antidepressants and antidepressant metabolites.

In some embodiments, the methods provided herein comprise adding one or more internal standards. In some embodiments, the one or more internal standards comprise deuterated internal standards. In some embodiments, the deuterated internal standards are selected from the group consisting of 1,3-chlorophenylpiperazine-D8, hydroxybupropion-D6, desmethyl-venlafaxine-D6, desmethylcitalopram-D3, trimipramine-D3, amitriptyline-D3, nortriptyline-D3, paroxetine-D6, protriptyline-D3, citalopram-D6, venlafaxine-D6, imipramine-D3, trazodone-D6, vilazodone-D4, and vortioxetine-D8.

In some embodiments, the sample comprises a biological sample. In a preferred embodiment, the sample is urine. In some embodiments, the sample is plasma or serum. In some embodiments, the sample is blood.

In some embodiments, the sample is subjected to liquid chromatography prior to ionization. In some embodiments, the liquid chromatography comprises high performance liquid chromatography.

In some embodiments, the method is capable of detecting antidepressants and antidepressant metabolites at levels within the range of about 4 ng/mL to about 5000 ng/mL, inclusive.

In some embodiments, the method is capable of detecting antidepressants and antidepressant metabolites at levels within the range of about 25 ng/mL to about 5000 ng/mL, inclusive.

In some embodiments, the mass spectrometry is tandem mass spectrometry. In some embodiments, the tandem mass spectrometry is conducted by selected reaction monitoring, multiple reaction monitoring, precursor ion scanning, or product ion scanning.

In a preferred embodiment, the tandem mass spectrometry is conducted by selected reaction monitoring.

In some embodiments, provided herein are determining the antidepressants and antidepressant metabolites comprising detecting ions comprising the following mass/charge ratios (m/z).

| | Precursor Q1 (m/z) | Fragment Q3 (m/z) | Analyte |
|---|---|---|---|
| 1 | 196.993 | 118 | 1,3-Chlorphenylpiperazine 1 |
| 2 | 196.993 | 119.1 | 1,3-Chlorphenylpiperazine 2 |
| 3 | 205.065 | 158.1 | 1,3-Chlorphenylpiperazine D8 |
| 4 | 278.096 | 105 | Amitriptyline 1 |
| 5 | 278.096 | 115 | Amitriptyline 2 |
| 6 | 281 | 202.1 | Amitriptyline-D3 |
| 7 | 314.006 | 271.1 | Amoxapine 1 |
| 8 | 314.006 | 193.1 | Amoxapine 2 |
| 9 | 256.02 | 130 | Hydroxybupropion 1 |
| 10 | 256.02 | 103 | Hydroxybupropion 2 |
| 11 | 262.061 | 130.1 | Hydroxybupropion-D6 |
| 12 | 325.07 | 109 | Citalopram 1 |
| 13 | 325.07 | 262.1 | Citalopram 2 |
| 14 | 331.103 | 109 | Citalopram-D6 |
| 15 | 264.083 | 91 | Nortriptyline 1 |
| 16 | 264.083 | 105 | Nortriptyline 2 |
| 17 | 267.095 | 105 | Nortriptyline-D3 |
| 18 | 311.043 | 109 | Desmethylcitalopram 1 |
| 19 | 311.043 | 262.1 | Desmethylcitalopram 2 |
| 20 | 314.072 | 108.9 | Desmethylcitalopram-D3 |
| 21 | 315.054 | 86.1 | Clomipramine 1 |
| 22 | 315.054 | 58 | Clomipramine 2 |
| 23 | 301.037 | 72 | Desmethylclomipramine 1 |
| 24 | 301.037 | 227.1 | Desmethylclomipramine 2 |
| 25 | 267.091 | 72 | Desipramine 1 |
| 26 | 267.091 | 193.1 | Desipramine 2 |
| 27 | 280.096 | 107 | Doxepin 1 |
| 28 | 280.096 | 165.1 | Doxepin 2 |
| 29 | 266.074 | 107 | Desmethyldoxapin 1 |
| 30 | 266.074 | 77 | Desmethyldoxapin 2 |
| 31 | 298.03 | 154.1 | Duloxetine 1 |
| 32 | 298.03 | 44.1 | Duloxetine 2 |
| 33 | 310.07 | 148.1 | Fluoxetine 1 |
| 34 | 310.07 | 44.1 | Fluoxetine 2 |
| 35 | 296.066 | 134.2 | Norfluoxetine 1 |
| 36 | 296.066 | 30.1 | Norfluoxetine 2 |
| 37 | 319.057 | 71 | Fluvoxamine 1 |
| 38 | 319.057 | 200.1 | Fluvoxamine 2 |
| 39 | 305.025 | 229.1 | Norfluvoxamine 1 |
| 40 | 305.025 | 188.1 | Norfluvoxamine 2 |
| 41 | 281.098 | 86 | Imipramine 1 |
| 42 | 281.098 | 58 | Imipramine 2 |
| 43 | 284.013 | 89 | Imipramine-D3 |
| 44 | 278.094 | 191.2 | Maprotiline 1 |
| 45 | 278.094 | 189 | Maprotiline 2 |
| 46 | 266.081 | 195.1 | Mirtazapine 1 |
| 47 | 266.081 | 194.1 | Mirtazapine 2 |
| 48 | 330.033 | 192.1 | Paroxetine 1 |
| 49 | 330.033 | 70 | Paroxetine 2 |
| 50 | 336.092 | 198.2 | Paroxetine-D6 |
| 51 | 264.096 | 191 | Protriptyline 1 |
| 52 | 264.096 | 189 | Protriptyline 2 |
| 53 | 267.095 | 191.1 | Protriptyline-D3 |
| 54 | 306 | 159 | Sertraline 1 |
| 55 | 306 | 275 | Sertraline 2 |
| 56 | 292.005 | 159 | Desmethylsertraline 1 |
| 57 | 292.005 | 123 | Desmethylsertraline 2 |
| 58 | 372.096 | 176.1 | Trazodone 1 |
| 59 | 372.096 | 148 | Trazodone 2 |
| 60 | 378.114 | 182.1 | Trazodone-D6 |
| 61 | 295.128 | 100.1 | Trimipramine 1 |
| 62 | 295.128 | 58.1 | Trimipramine 2 |
| 63 | 298.138 | 103.1 | Trimipramine-D3 |
| 64 | 278.126 | 58 | Venlafaxine 1 |
| 65 | 278.126 | 121 | Venlafaxine 2 |
| 66 | 284.139 | 64.1 | Venlafaxine-D6 |
| 67 | 264.106 | 58 | Desmethylvenlafaxine 1 |
| 68 | 264.106 | 107 | Desmethylvenlafaxine 2 |
| 69 | 270.134 | 64.1 | Desmethylvenlafaxine-D6 |
| 70 | 442.133 | 155.1 | Vilazodone 1 |
| 71 | 442.133 | 197.2 | Vilazodone 2 |
| 72 | 446.163 | 155.1 | Vilazodone-D4 |
| 73 | 299.059 | 150 | Vortioxetine 1 |
| 74 | 299.059 | 109 | Vortioxetine 2 |
| 75 | 307.082 | 153.1 | Vortioxetine-D8 |

In some embodiments, the methods described herein are capable of detecting antidepressants and antidepressant metabolites at levels within the range of 4 ng/mL to 5000 ng/mL, inclusive. In some embodiments, the methods described herein are capable of detecting antidepressants and antidepressant metabolites at levels within the range of 25 ng/mL to 5000 ng/mL, inclusive.

In some embodiments, the methods described herein are capable of quantitating antidepressants and antidepressant metabolites at lower limit of 10 ng/mL. In some embodiments, the methods described herein are capable of quantitating antidepressants and antidepressant metabolites at lower limit of 50 ng/mL.

In some embodiments, the sample is subjected to an extraction column, such as a solid phase extraction (SPE) column, prior to ionization. In some related embodiments, SPE and mass spectrometry are conducted with on-line processing.

In some embodiments, the sample is subjected to an analytical column, such as a high performance liquid chromatography (HPLC) column, prior to ionization. In some related embodiments, HPLC and mass spectrometry are conducted with on-line processing.

In some embodiments, the methods may be used to determine the presence or amount of antidepressants and antidepressant metabolites in a biological sample; such as plasma or serum. In some related embodiments, a biological sample is processed by one or more steps to generate a processed sample, which may then be subjected to mass spectrometric analysis. In some embodiments, the one or more processing steps comprise one or more purification steps, such as protein precipitation, filtration, liquid-liquid extraction, solid phase extraction, liquid chromatography, any immunopurification process, or the like, and any combination thereof.

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI) or electrospray ionization (ESI), may be used in embodiments of the present invention. In certain embodiments, antidepressants and antidepressant metabolites are measured using positive ion mode.

In preferred embodiments, a separately detectable internal standard is provided in the sample, the amount of which is also determined in the sample. In these embodiments, all or a portion of both the analyte of interest and the internal standard present in the sample is ionized to produce a plurality of ions detectable in a mass spectrometer, and one or more ions produced from each are detected by mass spectrometry. In these embodiments, the presence or amount of ions generated from the analyte of interest may be related to the presence of amount of analyte of interest in the sample.

In other embodiments, the amount of the antidepressants and antidepressant metabolites in a sample may be determined by comparison to one or more external reference standards. Exemplary external reference standards include blank plasma or serum spiked with antidepressants and antidepressant metabolites or an isotopically labeled variant thereof.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "immunopurification" or "immunopurify" refers to a purification procedure that utilizes antibodies, including polyclonal or monoclonal antibodies, to enrich the one or more analytes of interest. Immunopurification can be performed using any of the immunopurification methods well known in the art. Often the immunopurification procedure utilizes antibodies bound, conjugated or otherwise attached to a solid support, for example a column, well, tube, gel, capsule, particle or the like. Immunopurification as used herein includes without limitation procedures often referred to in the art as immunoprecipitation, as well as procedures often referred to in the art as affinity chromatography.

As used herein, the term "immunoparticle" refers to a capsule, bead, gel particle or the like that has antibodies bound, conjugated or otherwise attached to its surface (either on and/or in the particle). In certain embodiments utilizing immunopurification, immunoparticles comprise sepharose or agarose beads. In alternative embodiments utilizing immunopurification, immunoparticles comprise glass, plastic or silica beads, or silica gel.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In some embodiments, the sample comprises a body fluid sample; preferably plasma or serum.

As used herein, the term "solid phase extraction" or "SPE" refers to a process in which a chemical mixture is separated into components as a result of an affinity of components dissolved or suspended in a solution (i.e., mobile phase) for a solid through or around which the solution is passed (i.e., solid phase). SPE, as used herein, is distinct from immunopurification in that the affinity of components in the mobile phase to the solid phase is the result of a chemical or physical interaction, rather than an immunoaffinity. In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., J Chromatogr A 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., Turbulent Flow Analysis: Measurement and Prediction, P. S. Bernard & J. M. Wallace, John Wiley & Sons, Inc., (2000); An Introduction to Turbulent Flow, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 µm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 5 μm in diameter.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated N2 gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., Anal. Chem. 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

DETAILED DESCRIPTION OF THE INVENTION

Figure 1:
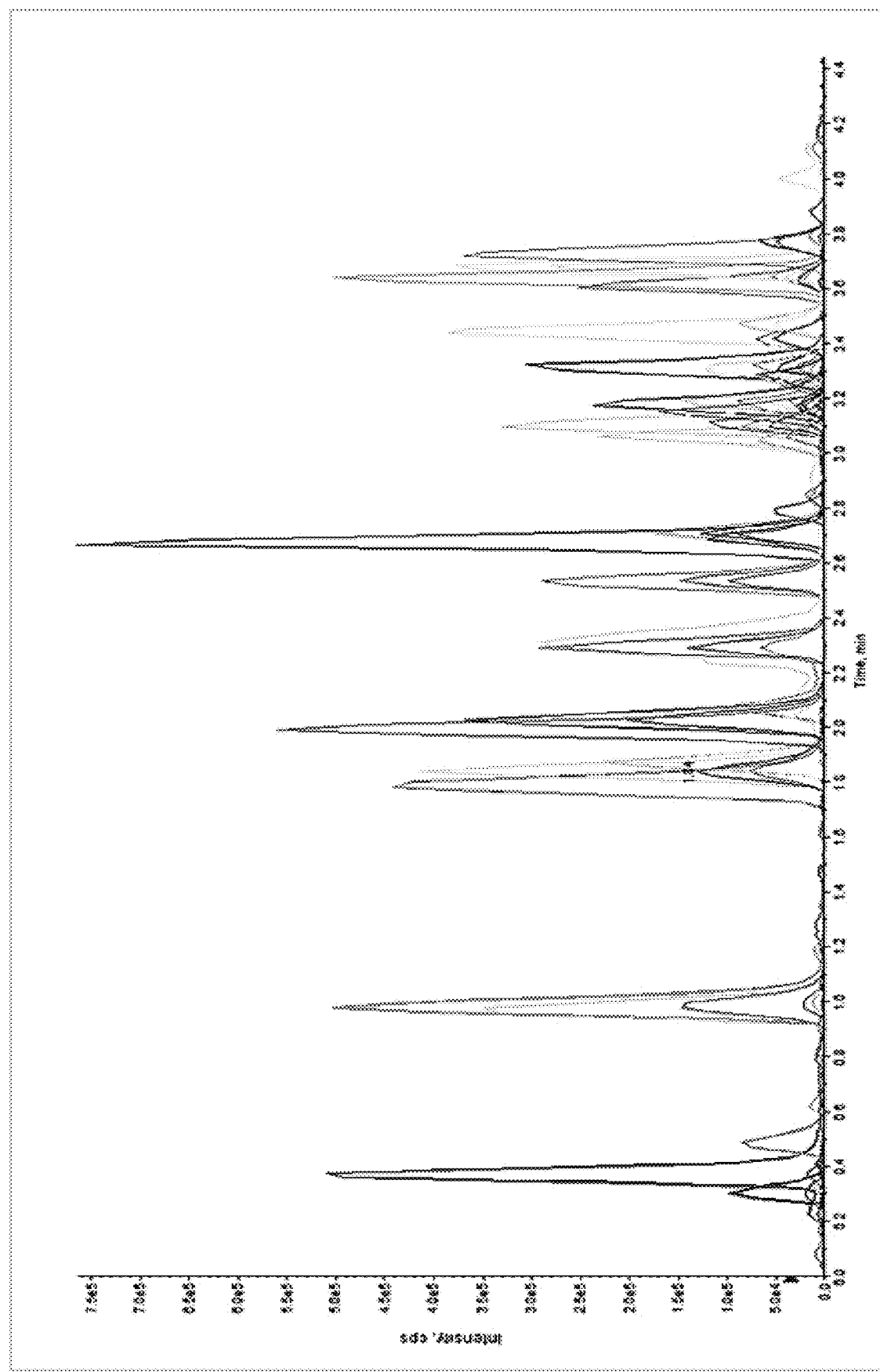
FIG. 1 shows LC-MS/MS profile of all analytes and metabolites.

In certain embodiments, antidepressant panels described herein can be used with compliance monitoring of patients having history/risk for use and or abuse of drugs within this class. Baseline testing, prior to prescribing this class of drugs, alerts the provider to the potential for polypharmacy drug conflicts. Compliance monitoring requires prescribed drugs to be present and absence of non-prescribed drugs for these patient populations.

Certain brain chemicals, neurotransmitters, are associated with depression, more specifically serotonin, norepinephrine and dopamine. Most antidepressants treat depression by affecting these neurotransmitters. Different types/classes of antidepressants affect these neurotransmitters in different ways. These types include: SSRIs, SNRIs, NDRIs, Tricyclic, Atypical, MAOIs, and others (see below).

Selective serotonin reuptake inhibitors (SSRIs). Doctors often start by prescribing an SSRI. These medications are safer and generally cause fewer bothersome side effects than other types of antidepressants. SSRIs include Fluoxetine (Prozac, Selfemra), Paroxetine (Paxil, Pexeva), Sertraline (Zoloft), Citalopram (Celexa), Escitalopram (Lexapro), Fluvoxamine (Faverin, Fevarin, Floxyfral, Dumyrox, Luvox), Vilazodone (Viibryd).

Serotonin and norepinephrine reuptake inhibitors (SNRIs)—duloxetine (Cymbalta), venlafaxine (Effexor XR), Desmethylvenlafaxine (synthetic form of venlafaxine's major metabolite, O-desmethylvenlafaxine; Pristiq, Khedezla) and levomilnacipran (Fetzima). SNRIs have unique dual action in raising levels of both serotonin and norepinephrine; therefore SNRI's combat more than one cause of depression.

Norepinephrine and dopamine reuptake inhibitors (NDRIs). Bupropion (Wellbutrin, Aplenzin, Forfivo XL) falls into this category. It's one of the few antidepressants not frequently associated with sexual side effects.

Tricyclic antidepressants (TCAs) tend to cause more side effects than newer antidepressants. Tricyclic antidepressants generally aren't prescribed unless the patient has tried an SSRI first without improvement. TCAs include imipramine (Tofranil), nortriptyline (Pamelor), amitriptyline (Elavil, Endep, Lentizol, Levate, Saroten, Tryptanol, Tryptizol), Doxepin (Adapin, Curatin, Silenor, Sinequan), Trimipramine (Surmontil), Desipramine (Norpramin), Protriptyline (Vivactil), Amoxapine (Asendin), Clomipramine (Anafranil), and Maprotiline (Ludiomil).

Atypical antidepressants. These medications don't fit neatly into any of the other antidepressant categories. They include Trazodone (Oleptro), Mirtazapine (Remeron) and Vortioxetine (Brintellix). These are sedating and usually taken in the evening.

Monoamine oxidase inhibitors (MAOIs) are not included in this assay. These medications can't be combined with SSRIs. Common MAOIs include tranylcypromine (Parnate), Phenelzine (Nardil) and Isocarboxazid (Marplan).

Methods are described for measuring the amount of analyte in a sample. More specifically, mass spectrometric methods are described for detecting and/or quantifying analyte in a biological sample, such as human plasma or serum. The methods may utilize liquid chromatography followed by tandem mass spectrometry to quantitate analyte in the sample.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as urine, blood, plasma, serum, saliva, cerebrospinal fluid, or tissue samples; preferably urine. Such samples may be obtained, for example, from a patient; that is, a living person, male or female, presenting oneself in a clinical setting for diagnosis, prognosis, or treatment of a disease or condition. In some embodiments, preferred samples may be obtained from female humans of childbearing potential. In embodiments where the sample comprises a biological sample, the methods may be used to determine the amount of leflunomide metabolite in the sample when the sample was obtained from the biological source (i.e., the amount of endogenous leflunomide metabolite in the sample).

The present invention also contemplates kits for antidepressant quantitation assay. A kit for antidepressant quantitation assay may include a kit comprising the compositions provided herein. For example, a kit may include packaging material and measured amounts of an isotopically labeled internal standard, in amounts sufficient for at least one assay. Typically, the kits will also include instructions recorded in a tangible form (e.g., contained on paper or an electronic medium) for using the packaged reagents for use in a antidepressant quantitation assay.

Calibration and QC pools for use in embodiments of the present invention are preferably prepared using a matrix similar to the intended sample matrix, provided that analyte is essentially absent.

Sample Preparation for Mass Spectrometric Analysis

In preparation for mass spectrometric analysis, analytes may be enriched relative to one or more other components in the sample (e.g. protein) by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a test sample, especially a biological test sample, such as serum or plasma. Protein purification methods are well known in the art. For example, Polson et al., *Journal of Chromatography B* 2003, 785:263-275, describes protein precipitation techniques suitable for use in methods of the present invention. Protein precipitation may be used to remove most of the protein from the sample leaving analytes in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to additional purification methods, such as liquid chromatography, and subsequent mass spectrometry analysis. In certain embodiments, the use of protein precipitation, such as for example, acetonitrile protein precipitation, may obviate the need for TFLC or other on-line extraction prior to mass spectrometry or high performance liquid chromatography (HPLC) and mass spectrometry.

Another method of sample purification that may be used prior to mass spectrometry is liquid chromatography (LC). Certain methods of liquid chromatography, including high performance liquid chromatography (HPLC), rely on relatively slow, laminar flow technology. Traditional HPLC analysis relies on column packing in which laminar flow of the sample through the column is the basis for separation of the analyte of interest from the sample. The skilled artisan will understand that separation in such columns is a partition process and may select LC, including HPLC, instruments and columns that are suitable for use with analytes. The chromatographic column typically includes a medium (i.e., a packing material) to facilitate separation of chemical moieties (i.e., fractionation). The medium may include minute particles. The particles typically include a bonded surface that interacts with the various chemical moieties to facilitate separation of the chemical moieties. One suitable bonded surface is a hydrophobic bonded surface such as an alkyl bonded, cyano bonded, or biphenyl bonded surface. Alkyl bonded surfaces may include C-4, C-8, C-12, or C-18 bonded alkyl groups. In preferred embodiments, the column is a biphenyl column. The chromatographic column includes an inlet port for receiving a sample and an outlet port for discharging an effluent that includes the fractionated sample. The sample may be supplied to the inlet port directly, or from a SPE column, such as an on-line extraction column or a TFLC column. In some embodiments, an on-line guard cartridge may be used ahead of the HPLC column to remove particulates and phospholipids in the samples prior to the samples reaching the HPLC column. In some embodiments, guard cartridge may be a biphenyl guard cartridge.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with a biphenyl column chromatographic system. In certain preferred embodiments, a biphenyl analytical column (e.g., a Pinnacle DB Biphenyl analytical column from Restek Inc. (5 μm particle size, 50×2.1 mm), or equivalent) is used. In certain preferred embodiments, HPLC is performed using HPLC Grade 0.1% aqueous formic acid as solvent A, and 0.1% formic acid in acetonitrile as solvent B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of analytes prior to mass spectrometry. In such embodiments, samples may be extracted using a TFLC column which captures the analyte. The analyte is then eluted and transferred on-line to an analytical HPLC column. For example, sample extraction may be accomplished with a TFLC extraction cartridge may be accomplished with a large particle size (50 μm) packed column. Sample eluted off of this column is then transferred on-line to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation by Mass Spectrometry

In various embodiments, analytes may be ionized by any method known to the skilled artisan. Mass spectrometry is performed using a mass spectrometer, which includes an ion source for ionizing the fractionated sample and creating charged molecules for further analysis. For example, ionization of the sample may be performed by electron ionization, chemical ionization, electrospray ionization (ESI), photon ionization, atmospheric pressure chemical ionization (APCI), photoionization, atmospheric pressure photoionization (APPI), laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

Analytes may be ionized in positive or negative mode. In some embodiments, analytes are ionized in positive mode.

In mass spectrometry techniques generally, after the sample has been ionized, the positively or negatively charged ions thereby created may be analyzed to determine a mass to charge ratio (m/z). Suitable analyzers for determining m/z include quadrupole analyzers, ion traps analyzers, and time-of-flight analyzers. Exemplary ion trap methods are described in Bartolucci, et al., *Rapid Commun. Mass Spectrom.* 2000, 14:967-73.

According to some methods of the present invention, high resolution/high accuracy mass spectrometry is used for quantitation of analytes. That is, mass spectrometry is conducted with a mass spectrometer capable of exhibiting a resolving power (FWHM) of at least 10,000, with accuracy of about 50 ppm or less for the ions of interest; preferably the mass spectrometer exhibits a resolving power (FWHM) of 20,000 or better and accuracy of about 20 ppm or less; such as a resolving power (FWHM) of 25,000 or better and accuracy of about 5 ppm or less; such as a resolving power (FWHM) of 25,000 or better and accuracy of about 3 ppm or less. Three exemplary mass spectrometers capable of exhibiting the requisite level of performance for analyte ions are those which include orbitrap mass analyzers, certain TOF mass analyzers, or Fourier transform ion cyclotron resonance mass analyzers.

Elements found in biological active molecules, such as carbon, oxygen, and nitrogen, naturally exist in a number of different isotopic forms. For example, most carbon is present as $^{12}C$, but approximately 1% of all naturally occurring carbon is present as $^{13}C$. Thus, some fraction of naturally occurring carbon containing molecules will contain at least one $^{13}C$ atom. Inclusion of naturally occurring elemental isotopes in molecules gives rise to multiple molecular isotopic forms. The difference in masses of molecular isotopic forms is at least 1 atomic mass unit (amu). This is because elemental isotopes differ by at least one neutron (mass of one neutron 1≈amu). When molecular isotopic forms are ionized to multiply charged states, the mass distinction between the isotopic forms can become difficult to discern because mass spectrometric detection is based on the mass to charge ratio (m/z). For example, two isotopic forms differing in mass by 1 amu that are both ionized to a 5+ state will exhibit differences in their m/z of only 0.2 (difference of 1 amu/charge state of 5). High resolution/high accuracy mass spectrometers are capable of discerning between isotopic forms of highly multiply charged ions (such as ions with charges of ±4, ±5, ±6, ±7, ±8, ±9, or higher).

Due to naturally occurring elemental isotopes, multiple isotopic forms typically exist for every molecular ion (each of which may give rise to a separately detectable spectrometric peak if analyzed with a sensitive enough mass spectrometric instrument). The m/z ratios and relative abundances of multiple isotopic forms collectively comprise an isotopic signature for a molecular ion. In some embodiments, the m/z and relative abundances of two or more molecular isotopic forms may be utilized to confirm the identity of a molecular ion under investigation. In some embodiments, the mass spectrometric peak from one or more isotopic forms is used to quantitate a molecular ion. In some related embodiments, a single mass spectrometric peak from one isotopic form is used to quantitate a molecular ion. In other related embodiments, a plurality of isotopic peaks are used to quantitate a molecular ion. In these later embodiments, the plurality of isotopic peaks may be subject to any appropriate mathematical treatment. Several mathematical treatments are known in the art and include, but are not limited to summing the area under multiple peaks or averaging the response from multiple peaks.

In mass spectrometry techniques generally, ions may be detected using several detection modes. For example, selected ions may be detected, i.e. using a selective ion monitoring mode (SIM), or alternatively, mass transitions resulting from collision activated dissociation (CAD), e.g., multiple reaction monitoring (MRM) or selected reaction monitoring (SRM). CAD is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy. Alternatively, neutral loss may be monitored.

In some embodiments, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the specificity of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of analytes. Methods of generating and using such standard curves are well known in the art and one of ordinary skill is capable of selecting an appropriate internal standard. For example, one or more forms of an isotopically labeled molecule with a similar m/z as analytes may be used as internal standards. In some embodiments described herein, an exemplary internal standard is an isotopically labeled diazepam, although numerous other compounds (isotopically labeled or otherwise) may be used. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium ($^2H$), $^{13}C$, and $^{15}N$. One or more isotopic labels can be incorporated at one or more positions in the molecule and one or more kinds of isotopic labels can be used on the same isotopically labeled molecule.

One or more steps of the methods may be performed using automated machines. In certain embodiments, one or more purification steps are performed on-line, and more preferably all of the purification and mass spectrometry steps may be performed in an on-line fashion.

In particularly preferred embodiments, analytes in a sample are detected and/or quantified using MS/MS as follows. Samples are preferably subjected to liquid chromatography, preferably HPLC; the flow of liquid solvent from a chromatographic column enters the heated nebulizer interface of an MS/MS analyzer; and the solvent/analyte mixture is converted to vapor in the heated charged tubing of the interface. During these processes, the analyte (i.e., antidepressants or metabolites) is analyzed. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of analytes. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. The fragment ions generated are passed into quadrupole 3 (Q3), where the fragment ions of analytes are selected while other ions are eliminated.

The methods may involve MS/MS performed in either positive or negative ion mode; preferably positive ion mode. Using standard methods well known in the art, one of ordinary skill is capable of identifying one or more fragment ions of a particular precursor ion of analytes that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of analytes. As described above, the relative abundance of a given ion may be converted into an absolute amount of the original analyte using calibration standard curves based on peaks of one or more ions of an internal or external molecular standard.

The following Examples serve to illustrate the invention. These Examples are in no way intended to limit the scope of the methods.

EXAMPLES

Example 1: Sample Preparation

We describe a validated LC-MS/MS method for simultaneous analysis for 23 prescribed antidepressant analytes and their metabolites provided in Table 1 below.

TABLE 1

Antidepressants and metabolites determined by the assay

| Name | Class | Brand Names |
|---|---|---|
| Amitriptyline | TCA | Elavil, Endep, Lentizol, Levate, Saroten, Tryptanol, Tryptizol |
| Amoxapine | TCA | Asendin |
| Citalopram/Escitalopram | SSRI | Celexa, Lexapro |
| Desmethylcitalopram-METABOLITE | | |
| Clomipramine | TCA | Anafranil |
| Desmethylclomipramine-METABOLITE | | |
| Desipramine | TCA | Norpramin |
| Doxepin | TCA | Adapin, Curatin, Silenor, Sinequan |
| Desmethyldoxepin-METABOLITE | | |
| Duloxetine | SNRI | Cymbalta |
| Fluoxetine | SSRI | Prozac, Selfemra |
| Norfluoxetine-METABOLITE | | |
| Fluvoxamine | SSRI | Faverin, Fevarin, Floxyfral, Dumyrox, Luvox |
| Norfluvoxamine-METABOLITE | | |
| Hydroxybupropion | NDRI | Wellbutrin, Aplenzin, Forfivo XL |
| Imipramine | TCA | Tofranil |
| Maprotiline | TCA | Ludiomil |
| Mirtazapine | Atypical | Remeron |
| Nortriptyline-METABOLITE of Amitriptyline & Prescribed Drug | TCA | Pamelor |
| Paroxetine | SSRI | Paxil, Pexeva |
| Protriptyline | TCA | Vivactil |

TABLE 1-continued

Antidepressants and metabolites determined by the assay

| Name | Class | Brand Names |
|---|---|---|
| Sertraline | SSRI | Zoloft |
| Norsertraline-METABOLITE | | |
| Trazodone | Atypical | Oleptro |
| 1,3-chlorphenylpiperazine (metaCPP)-METABOLITE | | |
| Trimipramine | TCA | Surmontil |
| Venlafaxine | SNRI | Effexor XR |
| O-Desmethylvenlafaxine-METABOLITE & Prescribed Drug | SNRI | Pristiq, Khedezla |
| Vilazodone | SSRI | Viibryd |
| Vortioxetine | Atypical | Brintellix |

Quality Controls, Calibrators, and Internal Standards: Calibration standards (4-5,000 ng/mL) and quality controls (QC's) at 5, 12.5, and 4,000 ng/mL were prepared by spiking stock solutions of analytes into drug-free urine controls (UTAK). The internal standard (IS) was a 25-100 ng/mL mixture of 1,3-chlorophenylpiperazine-D8, hydroxybupropion-D6, desmethyl-venlafaxine-D6, desmethylcitalopram-D3, trimipramine-D3, amitriptyline-D3, nortriptyline-D3, paroxetine-D6, protriptyline-D3, citalopram-D6, venlafaxine-D6, imipramine-D3, trazodone-D6, vilazodone-D4, and vortioxetine-D8.

Sample Preparation: Urine samples, calibrators, and QCs (25 µL each) were mixed with IS (25 µL) in a 1 mL, 96 well extraction plate, diluted with 450 µL of 10 mM ammonium formate in water (mobile phase A), and then vortexed at 1,100 rpm for 2 minutes before being moved to the LC-MS/MS for injection and analysis.

Example 2: Liquid Chromatography-Mass Spectrometry

Figure 2:
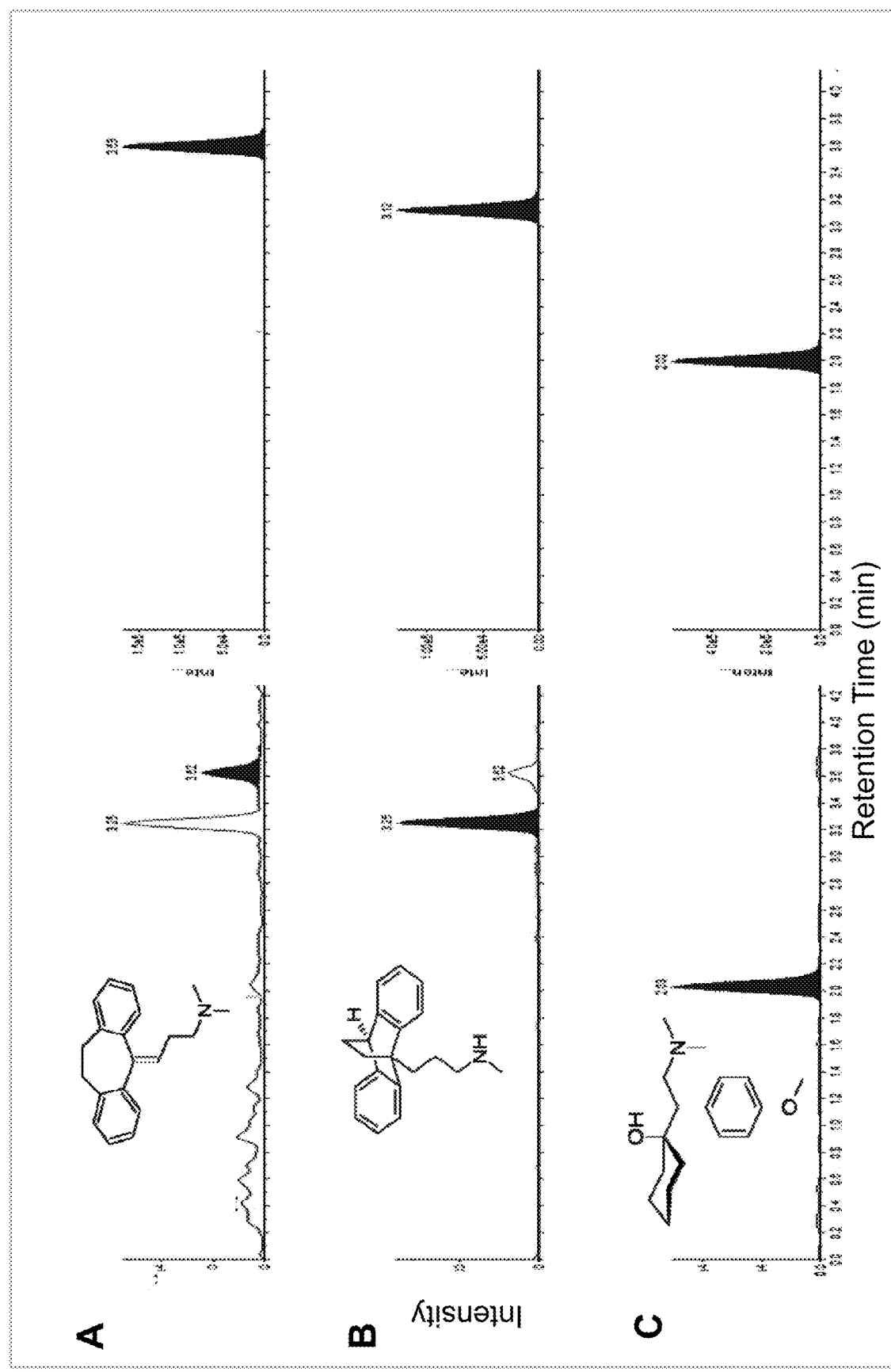
FIG. 2 shows an example of baseline separation of (A) amitriptyline, (B) maprotiline, and (C) venlafaxine (analytes: left, internal standard (IS): right).

LC-MS/MS: Extracted samples (25 µL) were chromatographically resolved on a Kinetex® Phenyl-Hexyl 50×4.6 mm 2.6µ column (Phenomenex) using mobile phase A/mobile phase B (25% methanol in acetonitrile) gradients. A 4-column LC multiplex was employed to maximize throughput on a Prelude LX-4 MD™ (ThermoFisher Scientific). A Sciex 4500 Triple Quad™ Mass Spectrometer was used for selected reaction monitoring. FIG. 1 is a representative chromatogram for all analytes, and FIG. 2 demonstrates baseline separation of closely related analytes.

Table 2 provides the mass transitions used to detect each analyte in the mass spectrometry assay.

TABLE 2

Mass spectrometry transitions (m/z) used for detecting antidepressants and metabolites

| | Q1 (m/z) | Q3 (m/z) | ID | DP | EP | CE | CXP |
|---|---|---|---|---|---|---|---|
| 1 | 196.993 | 118 | 1,3-Chlorphenylpiperazine 1 | 76 | 5 | 60 | 8 |
| 2 | 196.993 | 119.1 | 1,3-Chlorphenylpiperazine 2 | 76 | 5 | 45 | 10 |
| 3 | 205.065 | 158.1 | 1,3-Chlorphenylpiperazine D8 | 56 | 10 | 29 | 12 |
| 4 | 278.096 | 105 | Amitriptyline 1 | 81 | 10 | 50 | 10 |
| 5 | 278.096 | 115 | Amitriptyline 2 | 81 | 10 | 95 | 10 |
| 6 | 281 | 202.1 | Amitriptyline-D3 | 81 | 10 | 79 | 14 |
| 7 | 314.006 | 271.1 | Amoxapine 1 | 101 | 10 | 48 | 10 |
| 8 | 314.006 | 193.1 | Amoxapine 2 | 101 | 10 | 78 | 14 |
| 9 | 256.02 | 130 | Hydroxybupropion 1 | 56 | 10 | 85 | 12 |
| 10 | 256.02 | 103 | Hydroxybupropion 2 | 56 | 10 | 53 | 10 |
| 11 | 262.061 | 130.1 | Hydroxybupropion-D6 | 1 | 10 | 65 | 10 |
| 12 | 325.07 | 109 | Citalopram 1 | 81 | 10 | 90 | 10 |
| 13 | 325.07 | 262.1 | Citalopram 2 | 81 | 10 | 39 | 10 |
| 14 | 331.103 | 109 | Citalopram -D6 | 76 | 10 | 33 | 10 |
| 15 | 264.083 | 91 | Nortriptyline 1 | 76 | 10 | 70 | 8 |

TABLE 2-continued

Mass spectrometry transitions (m/z) used for detecting antidepressants and metabolites

|    | Q1 (m/z) | Q3 (m/z) | ID | DP | EP | CE | CXP |
|----|----------|----------|-----|-----|-----|-----|-----|
| 16 | 264.083  | 105      | Nortriptyline 2         | 76  | 10 | 45  | 10 |
| 17 | 267.095  | 105      | Nortriptyline-D3        | 71  | 10 | 27  | 10 |
| 18 | 311.043  | 109      | Desmethylcitalopram 1   | 81  | 10 | 85  | 10 |
| 19 | 311.043  | 262.1    | Desmethylcitalopram 2   | 81  | 10 | 36  | 10 |
| 20 | 314.072  | 108.9    | Desmethylcitalopram-D3  | 81  | 10 | 31  | 10 |
| 21 | 315.054  | 86.1     | Clomipramine 1          | 81  | 10 | 55  | 8  |
| 22 | 315.054  | 58       | Clomipramine 2          | 81  | 10 | 30  | 16 |
| 23 | 301.037  | 72       | Desmethylclomipramine 1 | 76  | 10 | 60  | 8  |
| 24 | 301.037  | 227.1    | Desmethylclomipramine 2 | 76  | 10 | 51  | 16 |
| 25 | 267.091  | 72       | Desipramine 1           | 71  | 5  | 55  | 10 |
| 26 | 267.091  | 193.1    | Desipramine 2           | 71  | 5  | 60  | 14 |
| 27 | 280.096  | 107      | Doxepin 1               | 76  | 10 | 55  | 10 |
| 28 | 280.096  | 165.1    | Doxepin 2               | 76  | 5  | 95  | 14 |
| 29 | 266.074  | 107      | Desmethyldoxapin 1      | 66  | 10 | 52  | 10 |
| 30 | 266.074  | 77       | Desmethyldoxapin 2      | 66  | 10 | 90  | 8  |
| 31 | 298.03   | 154.1    | Duloxetine 1            | 11  | 5  | 8   | 8  |
| 32 | 298.03   | 44.1     | Duloxetine 2            | 11  | 5  | 90  | 9  |
| 33 | 310.07   | 148.1    | Fluoxetine 1            | 16  | 5  | 13  | 10 |
| 34 | 310.07   | 44.1     | Fluoxetine 2            | 16  | 5  | 13  | 9  |
| 35 | 296.066  | 134.2    | Norfluoxetine 1         | 17  | 5  | 13  | 10 |
| 36 | 296.066  | 30.1     | Norfluoxetine 2         | 10  | 5  | 35  | 8  |
| 37 | 319.057  | 71       | Fluvoxamine 1           | 16  | 5  | 33  | 8  |
| 38 | 319.057  | 200.1    | Fluvoxamine 2           | 16  | 5  | 31  | 8  |
| 39 | 305.025  | 229.1    | Norfluvoxamine 1        | 1   | 5  | 23  | 10 |
| 40 | 305.025  | 188.1    | Norfluvoxamine 2        | 1   | 5  | 27  | 8  |
| 41 | 281.098  | 86       | Imipramine 1            | 66  | 10 | 60  | 8  |
| 42 | 281.098  | 58       | Imipramine 2            | 66  | 10 | 115 | 6  |
| 43 | 284.013  | 89       | Imipramine-D3           | 66  | 10 | 21  | 8  |
| 44 | 278.094  | 191.2    | Maprotiline 1           | 81  | 10 | 65  | 8  |
| 45 | 278.094  | 189      | Maprotiline 2           | 81  | 10 | 105 | 14 |
| 46 | 266.081  | 195.1    | Mirtazapine 1           | 86  | 10 | 60  | 14 |
| 47 | 266.081  | 194.1    | Mirtazapine 2           | 135 | 10 | 67  | 7  |
| 48 | 330.033  | 192.1    | Paroxetine 1            | 106 | 10 | 29  | 8  |
| 49 | 330.033  | 70       | Paroxetine 2            | 106 | 10 | 70  | 8  |
| 50 | 336.092  | 198.2    | Paroxetine-D6           | 71  | 10 | 29  | 8  |
| 51 | 264.096  | 191      | Protriptyline 1         | 81  | 10 | 55  | 16 |
| 52 | 264.096  | 189      | Protriptyline 2         | 81  | 10 | 95  | 14 |
| 53 | 267.095  | 191.1    | Protriptyline-D3        | 86  | 10 | 39  | 14 |
| 54 | 306      | 159      | Sertraline 1            | 66  | 5  | 39  | 10 |
| 55 | 306      | 275      | Sertraline 2            | 66  | 5  | 17  | 12 |
| 56 | 292.005  | 159      | Desmethylsertraline 1   | 6   | 5  | 35  | 8  |
| 57 | 292.005  | 123      | Desmethylsertraline 2   | 6   | 5  | 67  | 10 |
| 58 | 372.096  | 176.1    | Trazodone 1             | 111 | 5  | 45  | 12 |
| 59 | 372.096  | 148      | Trazodone 2             | 111 | 5  | 70  | 12 |
| 60 | 378.114  | 182.1    | Trazodone-D6            | 116 | 10 | 33  | 14 |
| 61 | 295.128  | 100.1    | Trimipramine 1          | 1   | 10 | 55  | 10 |
| 62 | 295.128  | 58.1     | Trimipramine 2          | 1   | 10 | 115 | 6  |
| 63 | 298.138  | 103.1    | Trimipramine-D3         | 31  | 10 | 23  | 10 |
| 64 | 278.126  | 58       | Venlafaxine 1           | 1   | 10 | 90  | 16 |
| 65 | 278.126  | 121      | Venlafaxine 2           | 1   | 10 | 60  | 12 |
| 66 | 284.139  | 64.1     | Venlafaxine-D6          | 1   | 10 | 57  | 6  |
| 67 | 264.106  | 58       | Desmethylvenlafaxine 1  | 1   | 10 | 75  | 6  |
| 68 | 264.106  | 107      | Desmethylvenlafaxine 2  | 1   | 10 | 65  | 10 |
| 69 | 270.134  | 64.1     | Desmethylvenlafaxine-D6 | 1   | 10 | 49  | 6  |
| 70 | 442.133  | 155.1    | Vilazodone 1            | 151 | 5  | 95  | 12 |
| 71 | 442.133  | 197.2    | Vilazodone 2            | 151 | 5  | 45  | 8  |
| 72 | 446.163  | 155.1    | Vilazodone-D4           | 151 | 5  | 69  | 12 |
| 73 | 299.059  | 150      | Vortioxetine 1          | 126 | 10 | 44  | 7  |
| 74 | 299.059  | 109      | Vortioxetine 2          | 126 | 10 | 44  | 7  |
| 75 | 307.082  | 153.1    | Vortioxetine-D8         | 101 | 5  | 38  | 8  |
|    | 278.2    | 202.1    | Amitriptyline 3         | 50  | 10 | 35  | 5  |
|    | 310.1    | 117.1    | Fluoxetine 3            | 50  | 10 | 35  | 5  |
|    | 310.1    | 91.1     | Fluoxetine 4            | 50  | 10 | 35  | 5  |
|    | 310.1    | 259.1    | Fluoxetine 5            | 50  | 10 | 35  | 5  |
|    | 319.2    | 145.1    | Fluvoxamine 3           | 50  | 10 | 35  | 5  |
|    | 319.2    | 130.1    | Fluvoxamine 4           | 50  | 10 | 35  | 5  |
|    | 266.2    | 209.2    | Mirtazapine 3           | 50  | 10 | 35  | 5  |
|    | 330.1    | 135.1    | Paroxetine 3            | 50  | 10 | 35  | 5  |
|    | 330.1    | 109      | Paroxetine 4            | 50  | 10 | 35  | 5  |
|    | 264.2    | 155.2    | Protriptyline 3         | 50  | 10 | 35  | 5  |
|    | 264.2    | 178.2    | Protriptyline 4         | 50  | 10 | 35  | 5  |
|    | 306      | 129.1    | Sertraline 3            | 50  | 10 | 35  | 5  |
|    | 295.2    | 193.1    | Trimipramine 3          | 50  | 10 | 35  | 5  |
|    | 295.2    | 208.2    | Trimipramine 4          | 50  | 10 | 35  | 5  |
|    | 278.2    | 147.1    | Venlafaxine 3           | 50  | 10 | 35  | 5  |

TABLE 2-continued

Mass spectrometry transitions (m/z) used for detecting antidepressants and metabolites

| Q1 (m/z) | Q3 (m/z) | ID | DP | EP | CE | CXP |
|---|---|---|---|---|---|---|
| 278.2 | 91.1 | Venlafaxine 4 | 50 | 10 | 35 | 5 |
| 278.2 | 191.1 | Amitriptyline 4 | 50 | 10 | 35 | 5 |

Example 3: Validation and Results

Validation: The following characteristics were determined by standard laboratory methods: limit of quantification (LOQ), linearity (including upper limit of linearity [ULOL] with dilution), precision, accuracy, interference by over 150 different drugs, stability, extracted specimen stability, matrix effect, and carryover.

Linearity:

A 5-9 point calibration curve exhibited consistent linearity and reproducibility in the range of ±20% of their target with regression coefficient (r)>0.990.

The CVs were between 7.5% and 10%.

The analytical measurement range (AMR) for all antidepressants analytes and metabolites was 4 to 5,000 ng/mL, with an LOQ of 10 ng/ml (with 1 exception), and an ULOL of 50,000 ng/mL. The exception was the metabolite, norsertraline, with an AMR of 25 to 5,000 ng/mL and a LOQ of 50 ng/mL.

Precision:

A precision study over a 5 day period showed consistent results with a sigma value of greater than 3 for the low, middle and high level QC's.

Figure 3:
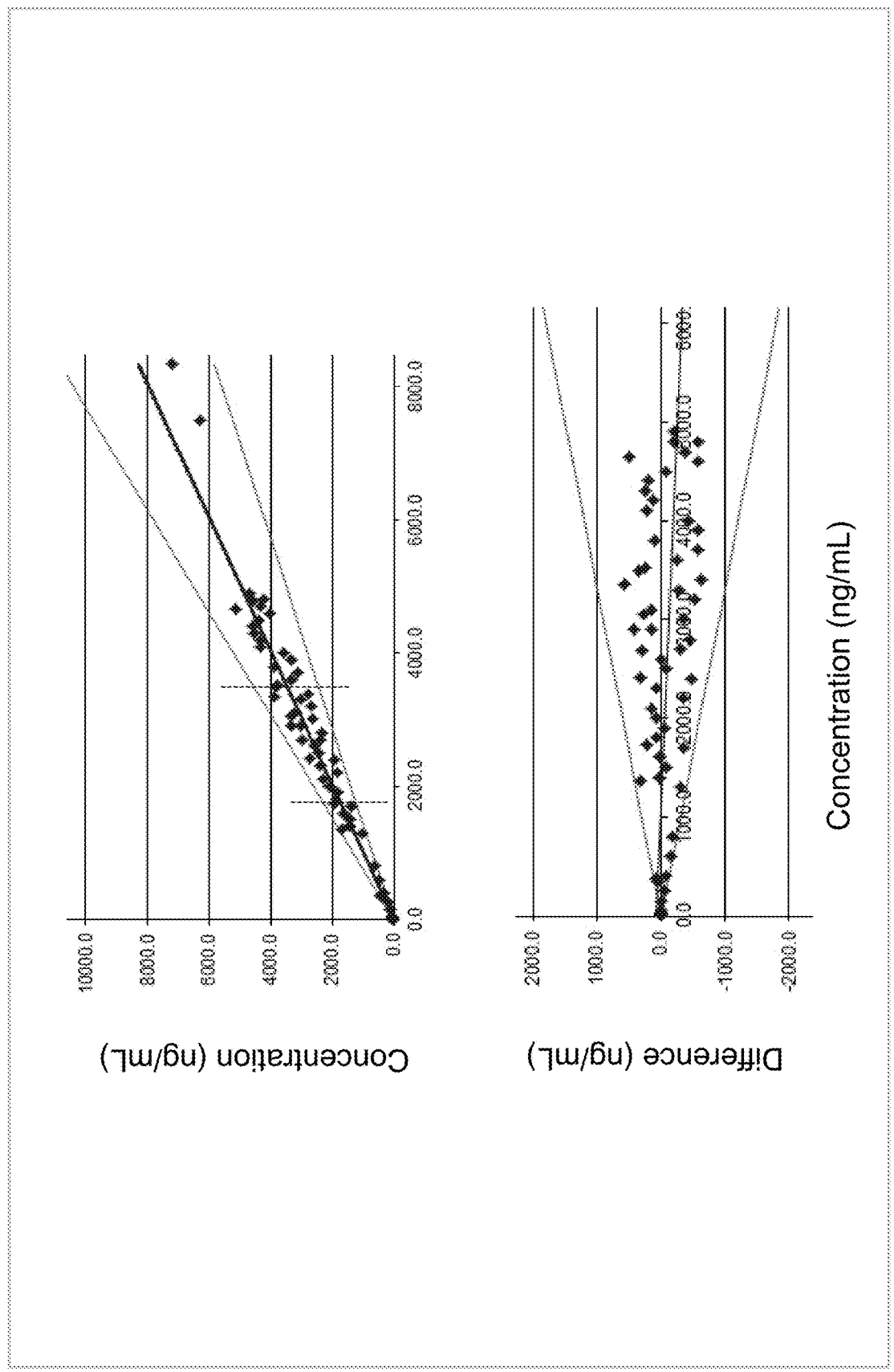
FIG. 3 shows accuracy of citalopram compared to another lab. Shows no bias greater than ±20% of values.
Figure 4:
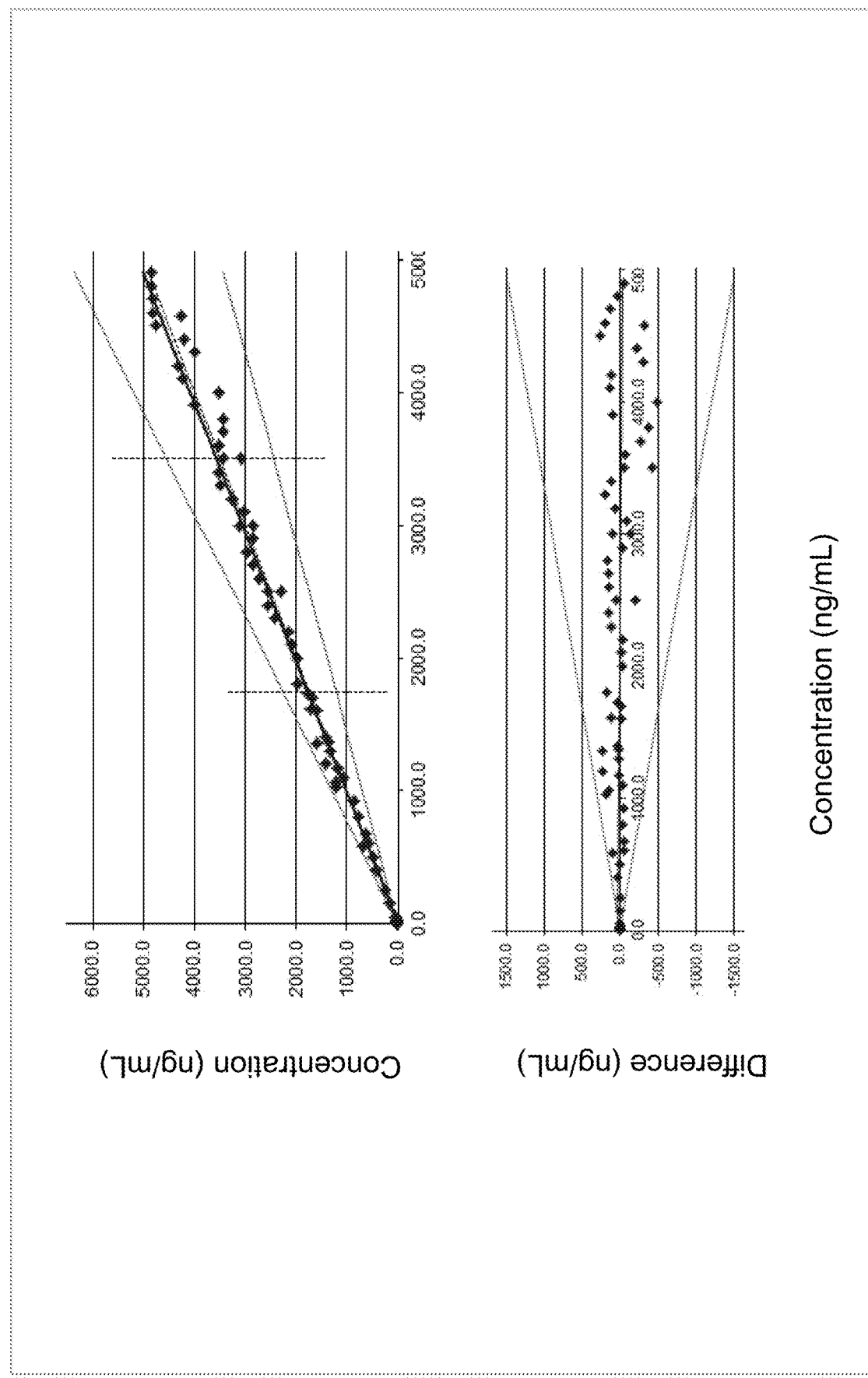
FIG. 4 shows accuracy of the metabolite desmethylcitalopram compared to another lab. Shows no bias greater than ±20% of values.
Figure 5:
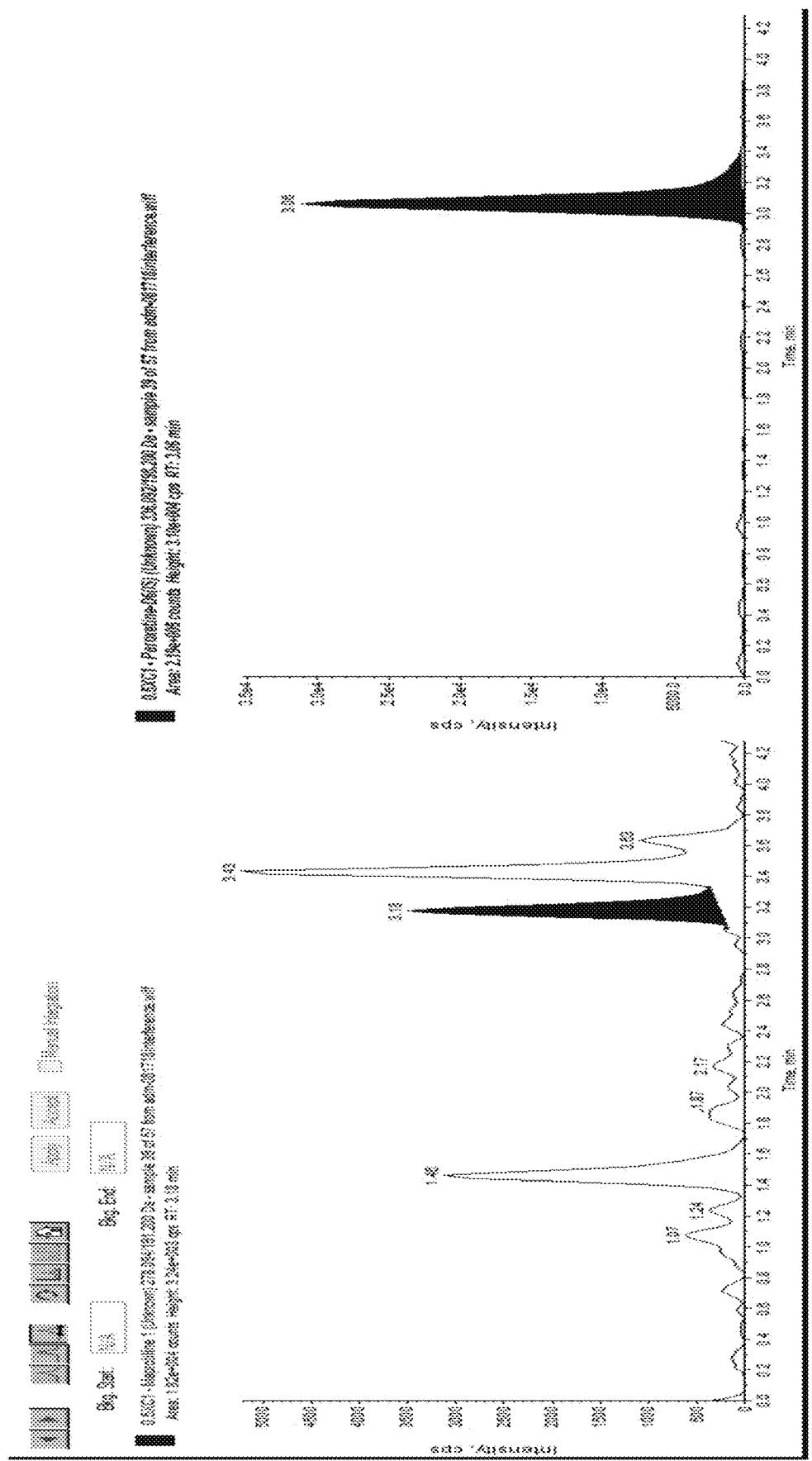
FIG. 5 shows Cyclobenzaprine interference separated. The figure shows 5 ng/mL Maprotiline+Cyclobenzaprine at 100×.
Figure 6:
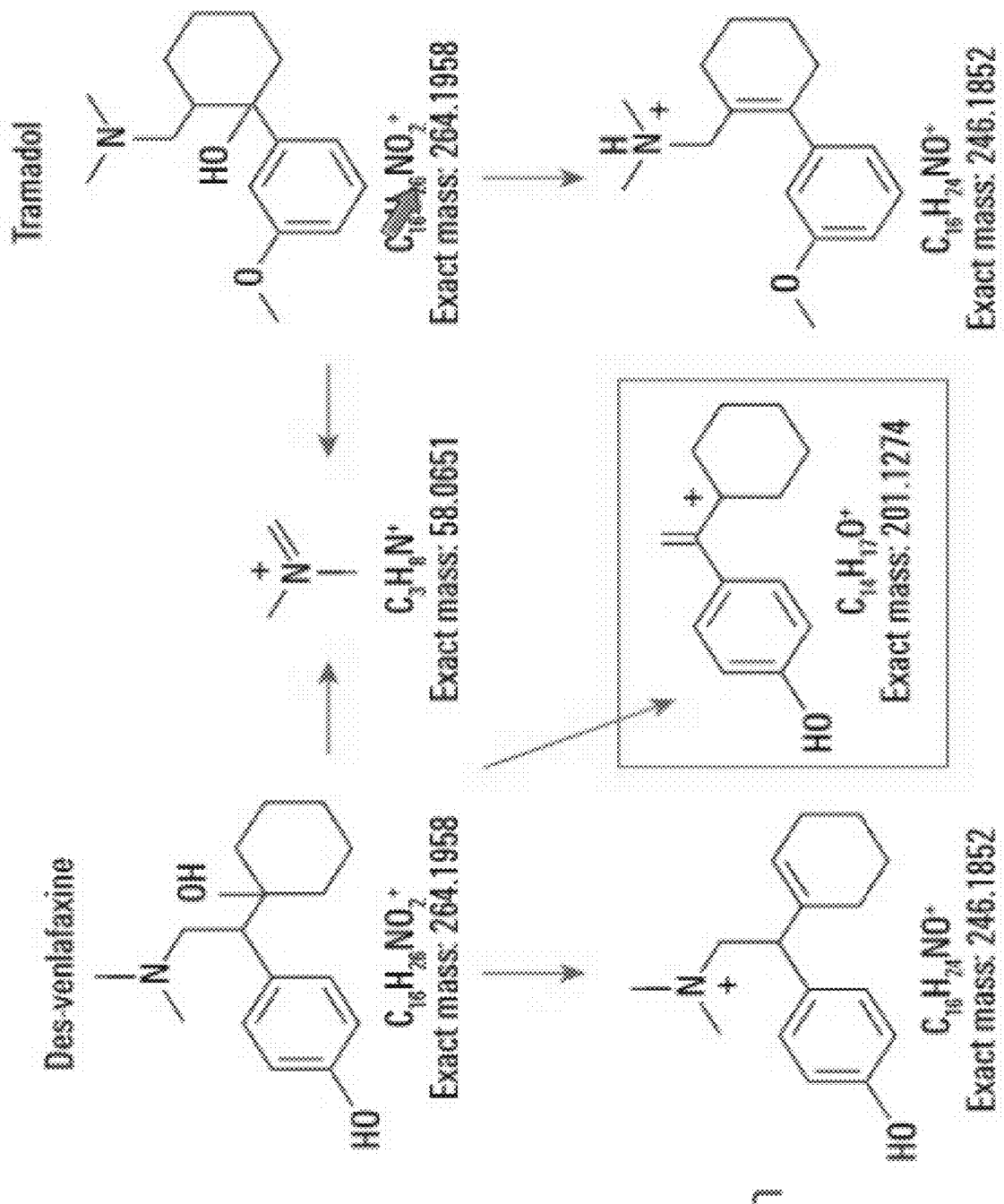
FIG. 6 shows mass spectral distinction of Desmethylvenlafaxine vs. Tramadol.
Figure 7:
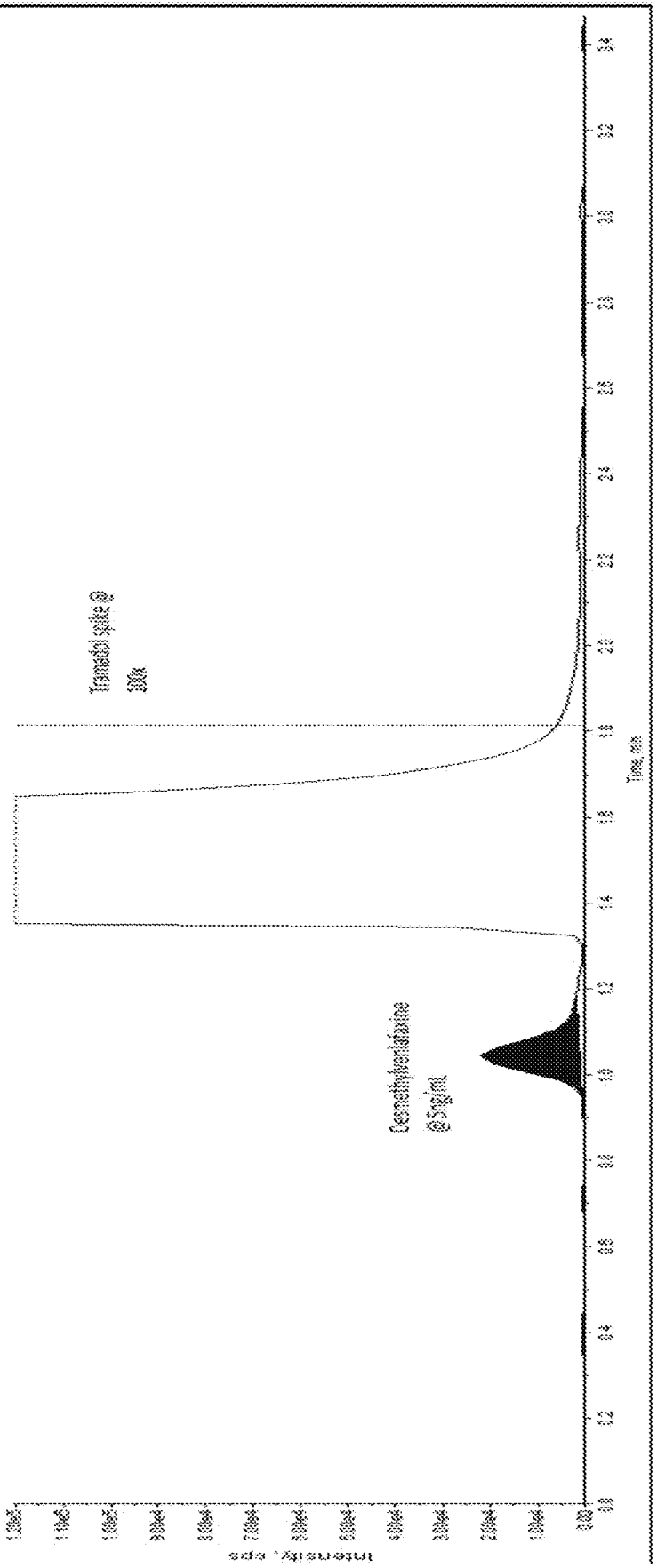
FIG. 7 shows Tramadol interference separated. The figure shows 5 ng/mL Desmethylvenlafaxine+Tramadol at 100×.
Figure 8:
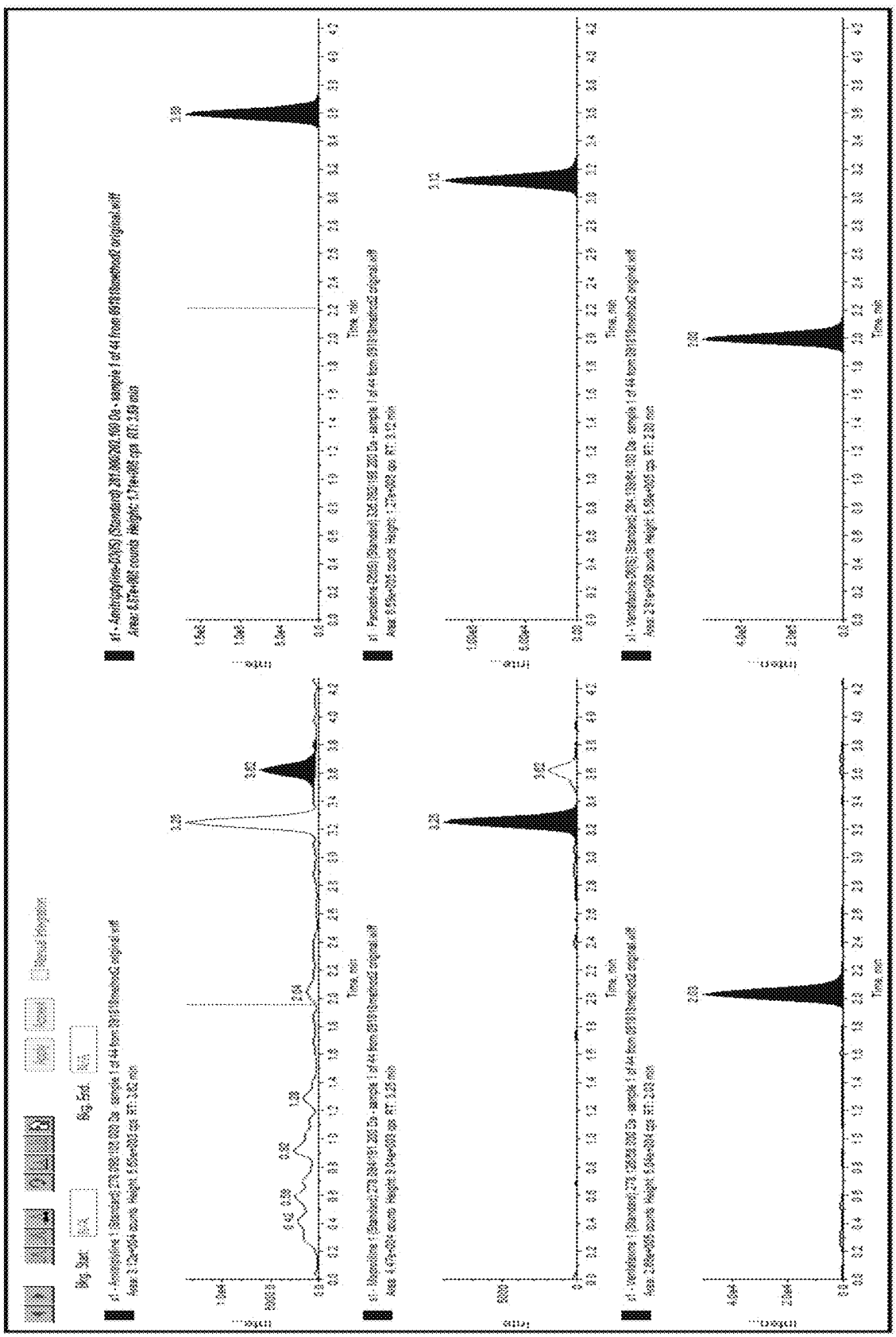
FIG. 8 shows Amitriptyline, Maprotiline, and Venlafaxine baseline separation.
Figure 9:
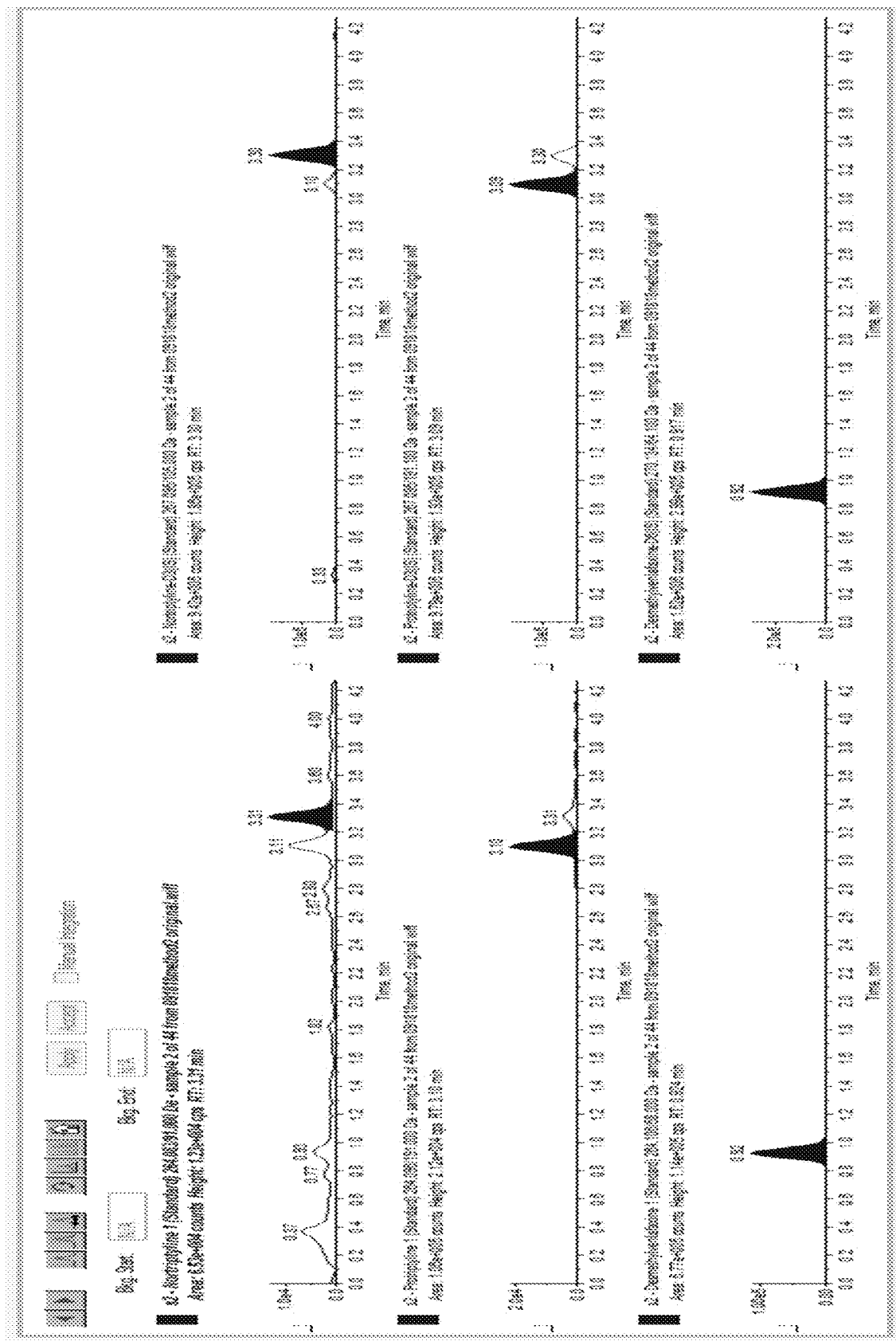
FIG. 9 shows Nortriptyline, Protriptyline, Desmethylvenlafaxine baseline separation.
Figure 10:
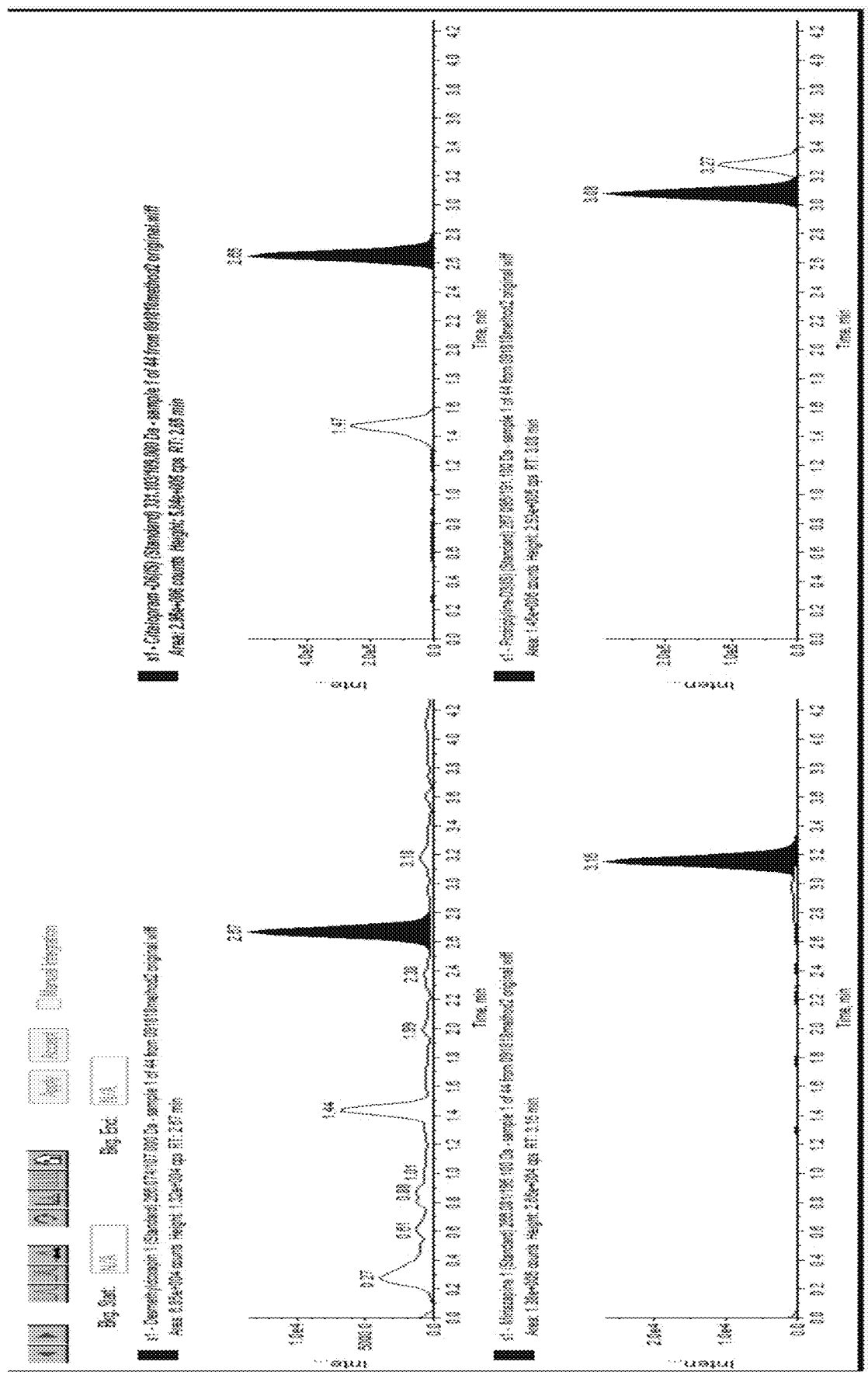
FIG. 10 shows Desmethyldoxepin and Mirtazapine baseline separation.
Figure 11:
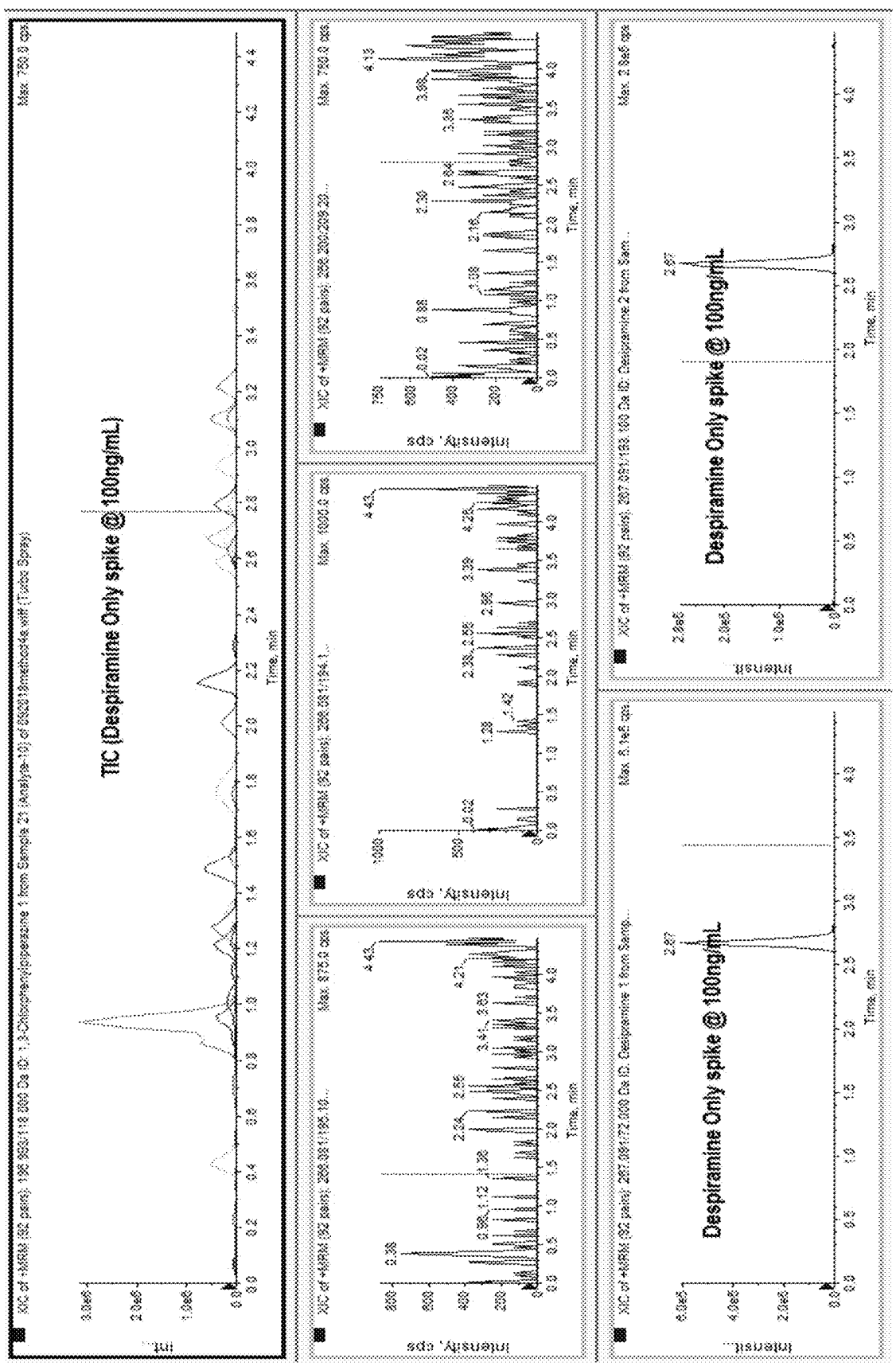
FIG. 11 shows Desipramine vs Mirtazapine Identified by different transitions.
Figure 12:
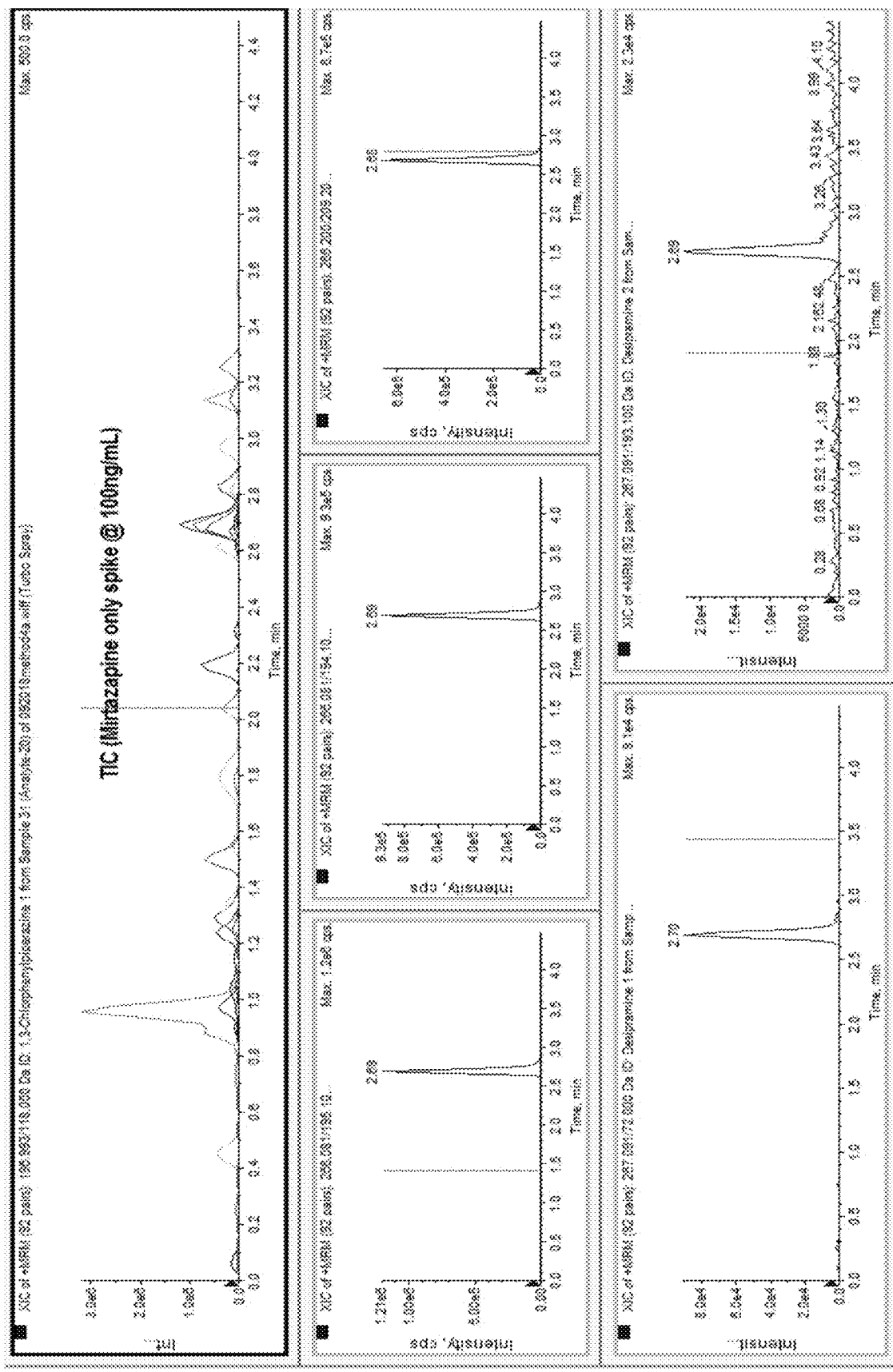
FIG. 12 shows ion ratio and/or relative retention time (RRT) will fail for Desipramine in patients positive for Mirtazapine.

Accuracy:

The accuracy study was carried out by correlating 65 sample across the concentration range of 4 to 20,000 ng/mL with another 65 results from another laboratory. Examples are presented in FIGS. 3 and 4.

On average, Deming regression showed a correlation coefficient of 1.022 and an intercept of −0.0681 with no bias.

Interference:

(Over 150 multiple illicit drugs and prescription drugs at 100 times the cutoff was tested. These tests were done using both in negative matrix control and LoQ control spiked with the relevant substances.)

None of the interference drugs tested cause ≥20% deviation in the signal intensities of the panel drugs at the LOQ.

Stability:

Specimens were stable for 7 days at room temperature, 14 days refrigerated, and 30 days frozen. Post-extraction, samples were stable for 24 hrs.

Matrix Effects:

Samples were compared at 3 different levels (0.5×, 2×, and 0.8×ULOL) with neat and diluted matrixes.

No matrix effects were observed.

Carryover:

Two samples were spiked at 4000 ng/mL back to back followed by 4 blank samples to determine carryover effects. This was ran in triplicate.

No carryover was observed.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

What is claimed is:

1. A method for simultaneously detecting or determining an amount of duloxetine, fluoxetine, and norfluoxetine in a biological sample by tandem mass spectrometry, the method comprising:
    subjecting a biological sample to ionization under conditions suitable to produce one or more ions detectable by mass spectrometry;
    determining the amount of one or more ions by tandem mass spectrometry, wherein the one or more ions comprise a norfluoxetine fragment ion with a mass-to-charge (m/z) ratio of 30.1±0.2; and
    using the amount of the one or more ions to determine the amount of duloxetine, fluoxetine, and norfluoxetine in the biological sample.

2. The method of claim 1, further comprising detecting or determining an amount of venlafaxine and/or desmethylvenlafaxine.

3. The method of claim 1, wherein the biological sample is subjected to liquid chromatography prior to ionization.

4. The method of claim 3, wherein the liquid chromatography comprises high performance liquid chromatography.

5. The method of claim 1, wherein the tandem mass spectrometry is conducted by selected reaction monitoring, multiple reaction monitoring, precursor ion scanning, or product ion scanning.

6. The method of claim 1, further comprising detecting or determining an amount of one or more of paroxetine, sertraline, norsertraline, citalopram, escitalopram, fluvoxamine, norfluvoxamine, vilazodone.

7. The method of claim 1, wherein the biological sample comprises urine.

8. The method of claim 1, wherein the biological sample comprises serum.

9. A method for detecting or determining an amount of norfluoxetine in a biological sample by tandem mass spectrometry, the method comprising:
   subjecting a biological sample to ionization under conditions suitable to produce a norfluoxetine fragment ion with a mass-to-charge (m/z) ratio of 30.1±0.2;
   determining an amount of the norfluoxetine fragment ion by tandem mass spectrometry; and
   determining the amount of norfluoxetine in the biological sample, wherein the amount of norfluoxetine is related to the amount of the norfluoxetine fragment ion.

10. The method of claim 9, further comprising detecting or determining an amount of one or more of fluoxetine, paroxetine, sertraline, norsertraline, citalopram, escitalopram, fluvoxamine, norfluvoxamine, or vilazodone.

11. The method of claim 9, further comprising detecting or determining an amount of one or more of duloxetine, venlafaxine, or desmethylvenlafaxine.

12. The method of claim 9, wherein the biological sample is subjected to liquid chromatography prior to ionization.

13. The method of claim 12, wherein the liquid chromatography comprises high performance liquid chromatography.

14. The method of claim 9, wherein the tandem mass spectrometry is conducted by selected reaction monitoring, multiple reaction monitoring, precursor ion scanning, or product ion scanning.

15. The method of claim 9, wherein the biological sample comprises urine.

16. The method of claim 9, wherein the biological sample comprises serum.

* * * * *